United States Patent
Cohen

(10) Patent No.: US 8,048,050 B2
(45) Date of Patent: Nov. 1, 2011

(54) ABSORBENT PAD

(75) Inventor: Richmond R. Cohen, Williamsport, PA (US)

(73) Assignee: First Quality Products, Inc., Great Neck, NY (US)

( * ) Notice: Subject to any disclaimer, the term of this patent is extended or adjusted under 35 U.S.C. 154(b) by 306 days.

(21) Appl. No.: 12/209,914

(22) Filed: Sep. 12, 2008

(65) Prior Publication Data

US 2010/0069870 A1 Mar. 18, 2010

(51) Int. Cl.
*A61F 13/15* (2006.01)
(52) U.S. Cl. ......... 604/385.04; 604/385.05; 604/385.03; 604/385.24; 604/385.28; 604/385.27
(58) Field of Classification Search ............. 604/385.04, 604/385.05, 385.03, 385.24, 385.28, 385.27
See application file for complete search history.

(56) References Cited

U.S. PATENT DOCUMENTS

2002/0007163 A1* 1/2002 Boulanger et al. ............ 604/366
2003/0023221 A1* 1/2003 Kashiwagi et al. ...... 604/385.04

* cited by examiner

*Primary Examiner* — Jacqueline F Stephens
(74) *Attorney, Agent, or Firm* — Amster, Rothstein & Ebenstein LLP

(57) ABSTRACT

An absorbent pad including: a main body having a first longitudinal edge and a second longitudinal edge, including: a liquid pervious topsheet; a liquid impervious backsheet; an absorbent layer disposed between the topsheet and the backsheet; a central adhesive element disposed on the backsheet and extending along a longitudinal centerline of the absorbent pad; and an elastic element disposed along each of the first and second longitudinal edges of the main body and attached to at least one of the topsheet and the backsheet; a first wing element extending from the backsheet and laterally beyond the first longitudinal edge of the main body; and a second wing element extending from the backsheet and laterally beyond the second longitudinal edge of the main body, the first and second wing elements being releasably attachable to an undergarment.

14 Claims, 4 Drawing Sheets

ABSORBENT PAD

FIELD OF THE INVENTION

The present invention relates to disposable absorbent pads having absorbent inserts, and more specifically to disposable absorbent pads having mechanisms for attachment to the user's undergarment.

BACKGROUND OF THE INVENTION

For convenience, discreetness and protection, women who are menstruating or who have very light incontinence issues may wear disposable absorbent articles such as pantiliners and sanitary napkins. When these women are ambulatory and/or wear the articles for long periods of time, the pads may shift from their original position and buckle, fold, or crumple. Further, the products may be distorted or twisted significantly and may even be dislodged completely. Such displacement, if it occurs prior to an episode of incontinence, may hinder the pad's ability to accept the bodily fluid from the user, which may result in leakage and wetness.

Conventional feminine pads, pantiliners and sanitary napkins are equipped with a backing strip of adhesive. The adhesive strip is pressed against the inside of the user's undergarment to hold the product in place during use. Although the adhesive provides considerable containment of the pad's position, it is not completely effective. The efficacy of the adhesive is compromised by the user's movement, particularly when the adhesive is exposed to wetness.

To provide improved stability, many feminine hygiene articles include wings to keep the articles in place. The wings are typically lateral extensions of the topsheet and backsheet materials extending from the crotch portion of the article. After the user attaches the backing strip to the undergarment, the wings may be folded back underneath the undergarment. The wings may overlap one another, and there may be at least one attachment means associated with at least one of the wings to secure the wings to one another on the underside of the undergarment. The attachment of the wings to the underside of the undergarment provides additional fastening to maintain the article in position during use.

Wings may be used in both feminine hygiene articles and bladder control pads. However, there are some risks associated with using such pads with wings for trapping and retaining urine, particularly during heavy periods of incontinence. In particular, because such pads with wings have lateral extensions of material beyond the crotch width of the pad, the wings preclude the use of any elastic means along the lateral crotch portions of the pads. Such elastic means assist in cupping and shaping the pads during use and are crucial in preventing leaks. Thus, since these bladder control pads with wings do not have elastic means, they are not particularly effective at retaining urine. Further, when the wings are deployed, the side edges of the pad are drawn away from the perineal area of the user, potentially encouraging more runoff after an episode of incontinence while wearing the pad.

SUMMARY OF THE INVENTION

An absorbent pad according to an exemplary embodiment of the present invention comprises: a main body having a first longitudinal edge and a second longitudinal edge, comprising: a liquid pervious topsheet; a liquid impervious backsheet; an absorbent layer disposed between the topsheet and the backsheet; a central adhesive element disposed on the backsheet and extending along a longitudinal centerline of the absorbent pad; and an elastic element disposed along each of the first and second longitudinal edges of the main body and attached to at least one of the topsheet and the backsheet; a first wing element extending from the backsheet and laterally beyond the first longitudinal edge of the main body; and a second wing element extending from the backsheet and laterally beyond the second longitudinal edge of the main body, the first and second wing elements being releasably attachable to an undergarment.

In at least one embodiment, the first and second wing elements are integrally formed with the backsheet.

In at least one embodiment, the first and second wing elements are attached to the backsheet.

In at least one embodiment, the absorbent pad further comprises a peel strip that covers the central adhesive.

In at least one embodiment, the absorbent system comprises an absorbent core.

In at least one embodiment, the absorbent system comprises an acquisition/distribution layer disposed over the absorbent core.

In at least one embodiment, the absorbent core comprises at least one of cellulosic fibers and superabsorbent material.

In at least one embodiment, the backsheet comprises an inner backsheet and an outer backsheet.

In at least one embodiment, the outer backsheet forms the first and second wing elements.

In at least one embodiment, the inner backsheet comprises a polymeric film layer.

In at least one embodiment, the outer backsheet comprises a nonwoven material.

In at least one embodiment, the topsheet comprises a nonwoven material.

A method of forming an absorbent pad according to an exemplary embodiment of the present invention comprises the steps of: forming a liquid pervious topsheet from a topsheet material web; forming a liquid impervious backsheet from a backsheet material web; forming a main body comprising an absorbent system disposed between the backsheet and the topsheet, the main body having a first longitudinal edge and a second longitudinal edge; attaching an elastic element to at least one of the topsheet and the backsheet along each of the first and second longitudinal edges of the main body, the elastic elements generating a cupping action so that the absorbent pad is biased towards a cup-like shape; attaching a central adhesive element to the backsheet along a longitudinal centerline of the absorbent pad; forming a first wing element on the backsheet, the first wing element extending laterally beyond the first longitudinal edge of the main body, and forming a second wing element on the backsheet, the second wing element extending laterally beyond the second longitudinal edge of the main body.

In at least one embodiment, the steps of forming first and second wings comprise forming first and second wings integrally with the backsheet.

In at least one embodiment, the steps of forming first and second wings comprise attaching first and second wings to the backsheet.

In at least one embodiment, the method further comprises the step of covering the central adhesive element with a central peel strip.

In at least one embodiment, the step of forming the main body comprises laminating the topsheet, backsheet and absorbent system together to form a unitary structure.

In at least one embodiment, the absorbent system comprises an absorbent core.

In at least one embodiment, the absorbent system comprises an acquisition/distribution layer disposed over the absorbent core.

In at least one embodiment, the topsheet material comprises a nonwoven material layer.

In at least one embodiment, the backsheet comprises an inner backsheet and an outer backsheet.

In at least one embodiment, the step of forming the first wing element comprises cutting the outer backsheet so that the outer backsheet extends laterally beyond the first longitudinal edge of the main body.

In at least one embodiment, wherein the step of forming the second wing element comprises cutting the outer backsheet so that the outer backsheet extends laterally beyond the second longitudinal edge of the main body.

In at least one embodiment, the step of forming the first and second wing elements comprises splitting the outer backsheet into a first portion and a second portion, the first portion extending laterally beyond the first longitudinal edge of the main body and the second portion extending laterally beyond the second longitudinal edge of the main body.

BRIEF DESCRIPTION OF THE DRAWINGS

The above and related objects, features and advantages of the present invention will be more fully understood by reference to the following detailed description of the presently preferred, albeit illustrative, embodiments of the present invention when taken in conjunction with the accompanying drawings wherein.

DETAILED DESCRIPTION OF PREFERRED EMBODIMENTS

The present invention is directed to an absorbent pad that has wing portions as well as elastic elements along the lateral side portions of the crotch area of the pad. Thus, the inventive absorbent pad may provide the added fastening capability provided by wings and the added leakage protection provided by elastic elements. Further, the structure of the absorbent pad according to various exemplary embodiments of the present invention is such that the deployment of the wings does not negate the benefits provided by the elastic elements. In other words, the structure of the present invention allows the wing portions and elastic elements to perform their intended function independently of each other.

Figure 1:
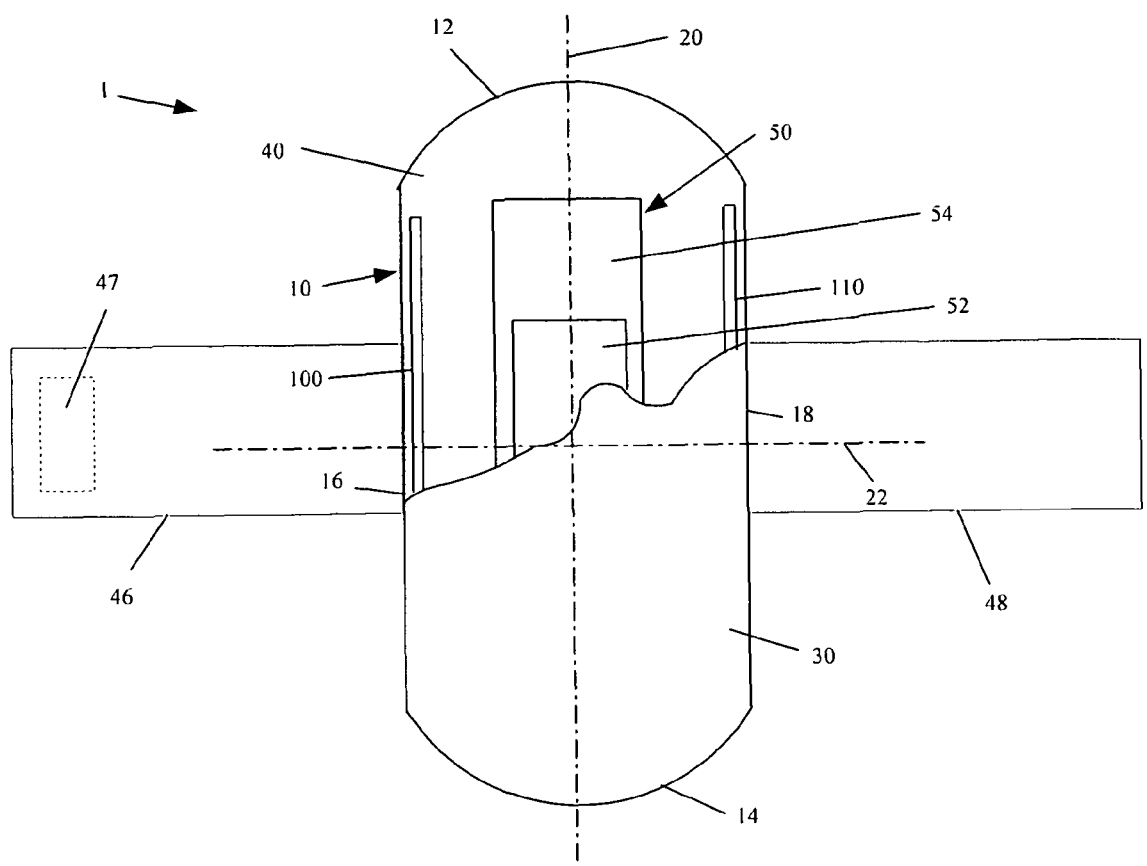
FIG. 1 is a top elevational view of an absorbent pad according to an exemplary embodiment of the present invention with the topsheet partially removed.
Figure 2A:
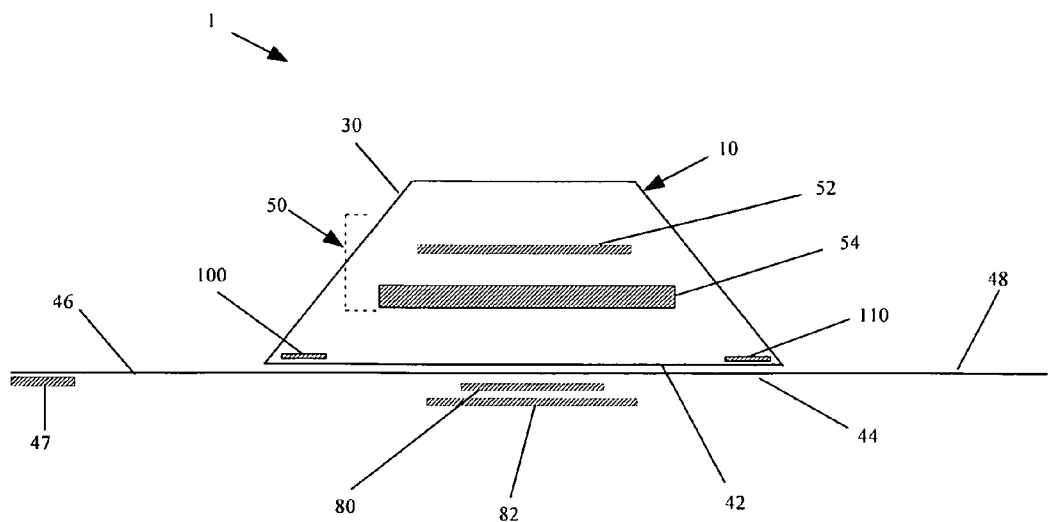
FIGS. 2A and B are cross-sectional views of an absorbent pad according to an exemplary embodiment of the present invention taken along the transverse centerline 22 in FIG. 1.
Figure 2B:
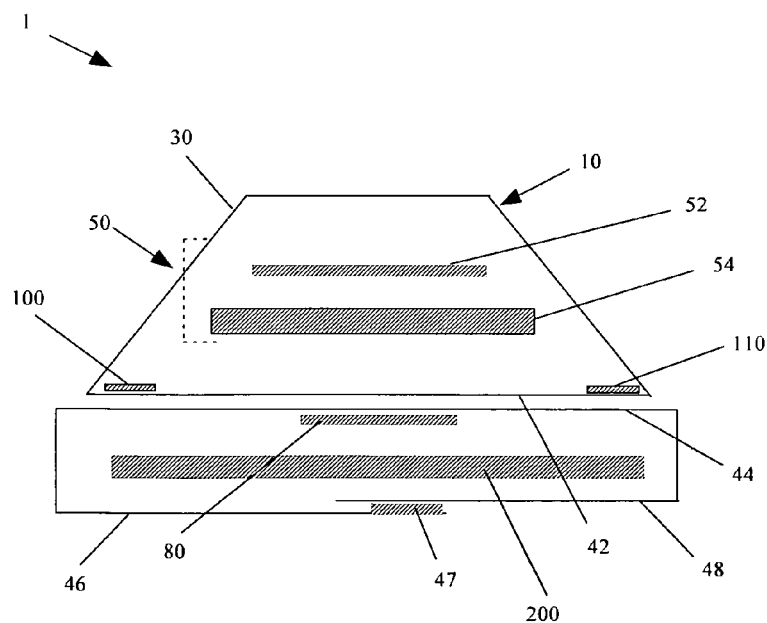
Figure 3A:
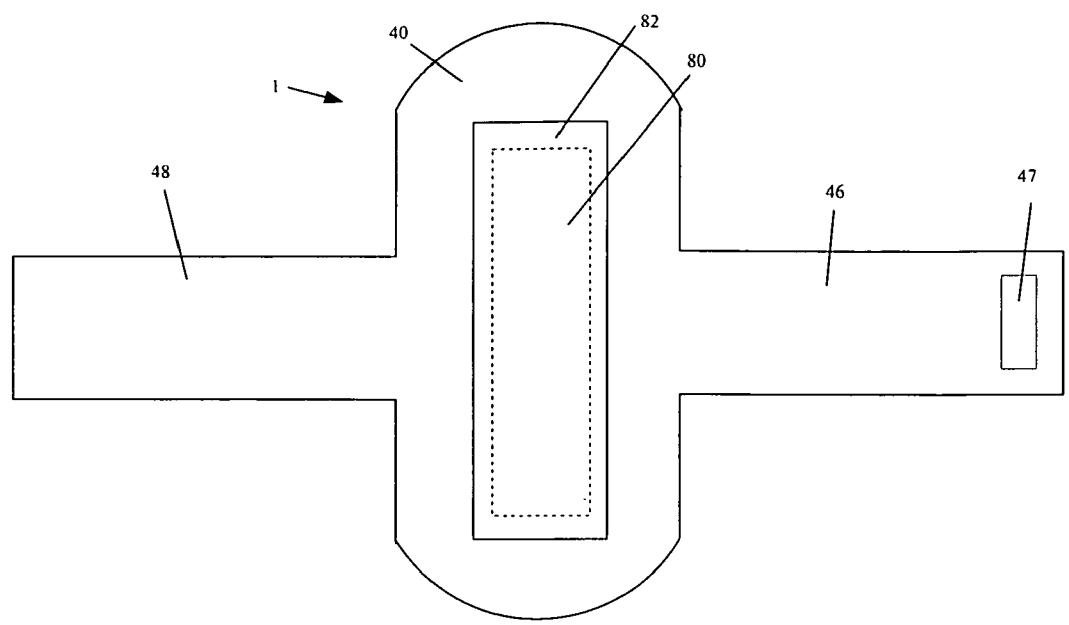
FIGS. 3A-C are bottom plan views of absorbent pads according to various exemplary embodiments of the present invention.
Figure 3B:
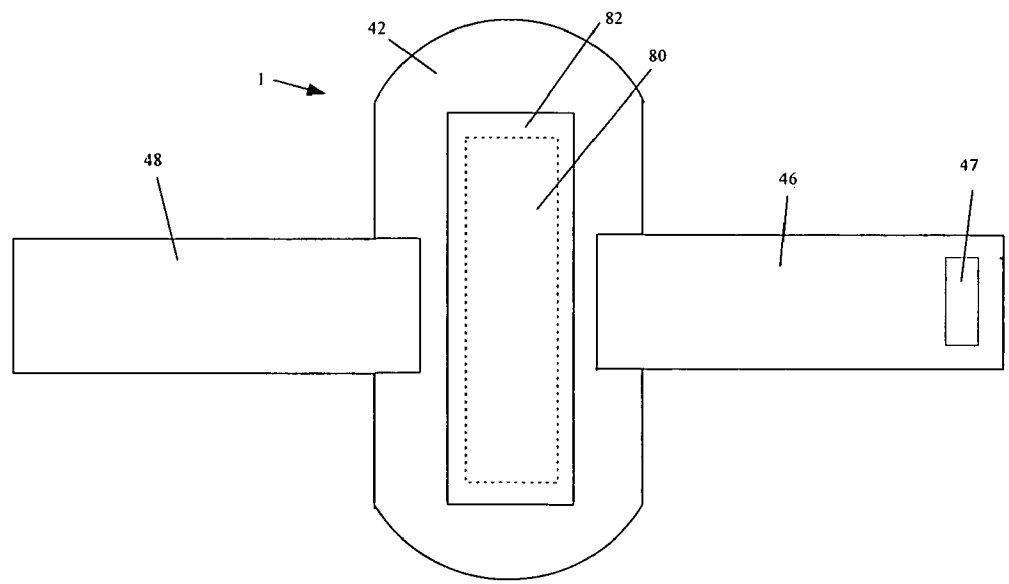
Figure 3C:
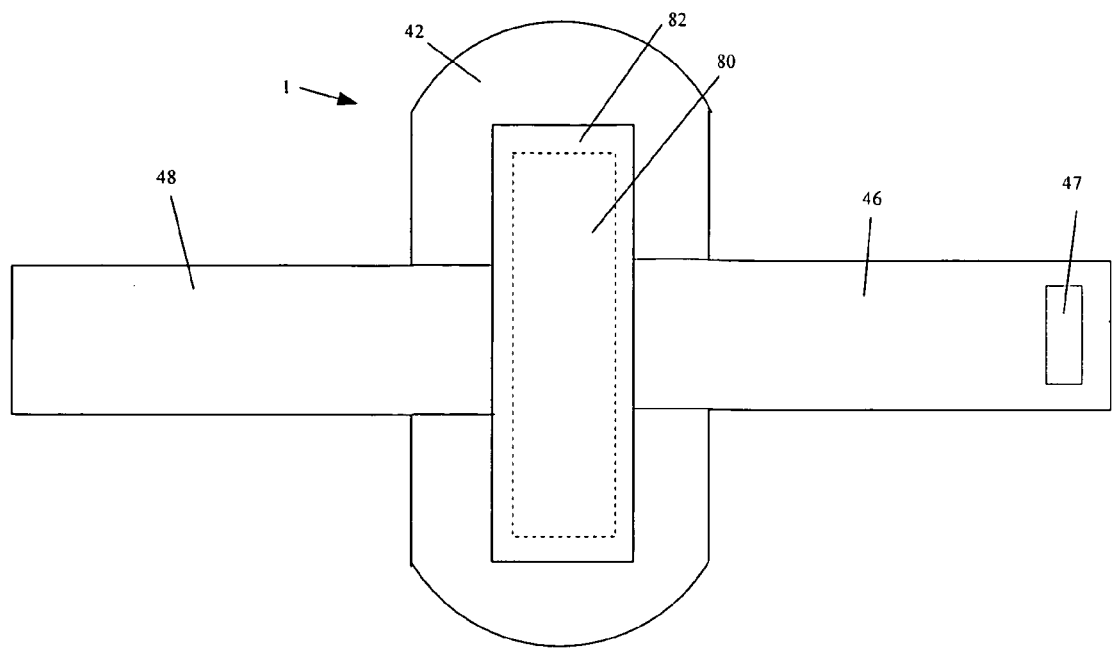
Figure 4:
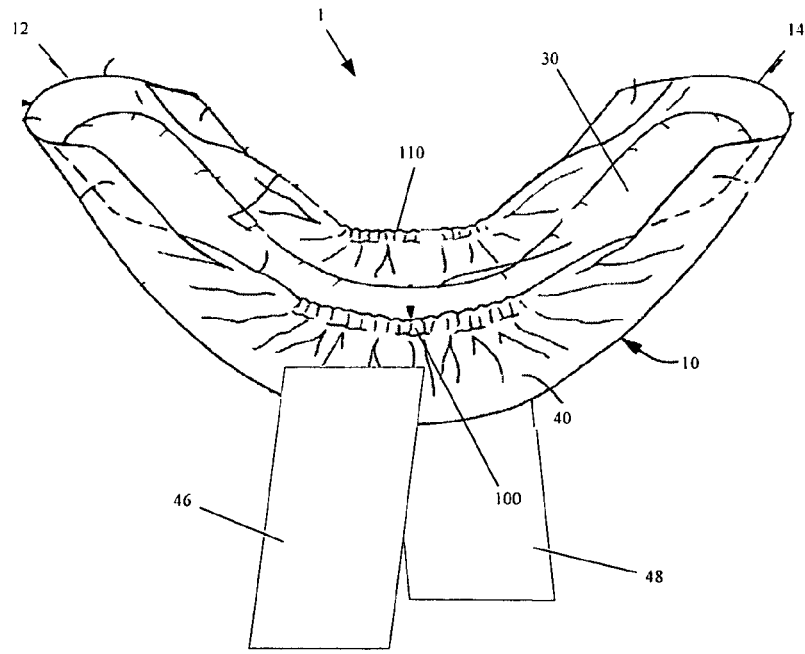
FIG. 4 is a perspective view of an absorbent pad according to an exemplary embodiment of the present invention having a cup-like configuration.

FIGS. 1-4 show the absorbent pad, generally designated by reference number 1, according to an exemplary embodiment of the present invention. FIG. 1 is a top elevational view of the absorbent pad 1 with the topsheet partially removed; FIG. 2A is a cross-sectional view of the absorbent pad 1 taken along the transverse centerline 22 in FIG. 1 with extended wings; FIG. 2B is a cross-sectional view of the absorbent pad 1 taken along the transverse centerline 22 in FIG. 1 with wings folded over one another and as attached to an undergarment 200; FIGS. 3A-C are bottom plan views of the absorbent pad 1 according to various exemplary embodiments; and FIG. 4 is a perspective view of the absorbent pad 1 having a cup-like configuration.

The absorbent pad 1 includes a main body 10 with a first transverse side 12 defining a front portion of the absorbent pad 1 and a second transverse side 14 defining a rear portion of the absorbent pad 1. Each of the first and second transverse sides 12, 14 are arcuate in shape. The main body 10 also has a first longitudinal side 16 and a second longitudinal side 18.

The absorbent pad 1 has an imaginary longitudinal centerline 20 bisecting the absorbent pad 1 in two identical halves and an imaginary transverse centerline 22 perpendicular to the longitudinal centerline 20.

As shown in FIGS. 1-4, the main body 10 is of a laminate construction and preferably includes a fluid-permeable topsheet 30, a fluid-impervious backsheet 40 and an absorbent system 50 disposed between the topsheet 30 and the backsheet 40. As explained in further detail below, each of these components may be made up of one or more layers.

As shown in FIG. 3, the bottom surface of the main body 10 includes a central adhesive element 80 extending substantially along the longitudinal centerline 20 of the main body 10. In the exemplary embodiment shown in FIG. 3, the transverse centerline 22 of the main body 10 bisects the central adhesive element 80 into two halves having equal lengths. Preferably, the central adhesive element 80 extends along substantially the entire longitudinal length of the main body 10. A central peel strip 82 may be applied to the central adhesive element 80 to protect the central adhesive element 80 prior to use. The central peel strip 82 may be made of, for example, siliconized paper.

The main body 10 further includes a first elastic element 100 extending parallel and immediately adjacent to the first longitudinal side 16, and a second elastic element 110 extending parallel and immediately adjacent to the second longitudinal side 18. When in their naturally contracted state, the first and second elastic elements 100, 110 cause a "cupping action", in that the absorbent pad 10 is pulled into a cup-like shape by the first and second elastic elements 100, 110. The first and second elastic elements 100, 110 may be composed of multiple elastic strands made of any suitable elastic material, such as, for example, synthetic rubber materials, elastic foams, elastic films, elastic nonwovens or other materials known in the art. Preferably, the first and second elastic elements 100, 110 are laminated between the topsheet 30 and the backsheet 40, and the elastic elements 100, 110 are attached to one or both of the topsheet 30 and the backsheet 40.

The backsheet 40 may be composed of a liquid-impervious film material so as to prevent liquid that is entrapped in the absorbent system 50 from egressing the absorbent pad 1 and staining the wearer's undergarment. The backsheet 40 is preferably made of polymeric film, although it may be made of liquid impervious, air-permeable material such as repellent-treated non-woven or micropore films or foams. Alternatively, the backsheet 40 may be made up of a nonwoven material laminated to a thin film material.

In a preferred embodiment, the backsheet 40 is made up of an inner backsheet 42 and an outer backsheet 44. The inner backsheet 42 may be made of a polymeric film and the outer backsheet 44 may be made of a nonwoven material. The outer backsheet 44 extends laterally beyond the first and second longitudinal sides 16, 18 of the main body 10 so as to form first and second wings 46, 48. In other exemplary embodiments of the present invention, the first and second wings 46, 48 are separately attached to the backsheet 40. Preferably, the first and second wings 46, 48 provide the absorbent pad 1 with a maximum width that is at least twice the maximum width of the main body 10. A male fastener element 47 may be disposed on the outer surface of the end portion of the first wing 46. The male fastener element 47 may be, for example, a hook fastener element. As explained in further detail below, the male fastener element 47 may be used to fasten the first and second wings 46, 48 to an undergarment as well as to each other. Alternatively, one or both of the first and second wings 46, 48 may include adhesive and/or fastener elements. In other exemplary embodiments of the present invention, the first and second wings 46, 48 may only be releasably attachable to the underside of the undergarment, and not to each other.

The functionality of the absorbent pad 1 will now be described. Prior to use, the first and second wings 46, 48 of the absorbent pad 1 may be folded over one another and fastened to one another via the fastener element 47 so that multiple absorbent pads may be conveniently stacked together and stored within a single package or a single absorbent pad may be stored in an individual package. A user may then remove the absorbent pad 1 from its package and, as shown in FIG. 4, suitably cup the pad to take full advantage of the elastic elements 100, 110 and unfasten the first and second wings 46, 48 from one another. Next, the user may remove the central peel strip 82 to expose the central adhesive 80. The absorbent pad 1 may then be firmly positioned onto the body side of the undergarment. As shown in FIG. 2B, the first and second wings 46, 48 may then be successively folded over the underside of the undergarment, with the first wing 46 fastened to the second wing 48 via the fastener element 47. The undergarment may then be pulled up close to the body, with the absorbent pad 1 positioned securely for leakage protection.

In various exemplary embodiments of the present invention, the outer backsheet 44 may be configured in a number of ways so as to form the first and second wings 46, 48 while also providing cost savings by preserving backsheet material. For example, as alternatives to the embodiment shown in FIG. 3A, in which the outer backsheet 44 extends across the full length and width of the absorbent pad 1, the outer backsheet 44 may be split into separate sections that form the first and second wings 46, 48 (FIG. 3B), or the outer backsheet 44 may be cut along its cross direction and placed only across the width of the absorbent pad 1 to form the first and second wings (FIG. 3C).

The topsheet 30 may be a relatively low density, bulky, high-loft nonwoven web material. The nonwoven may be spunbond, meltblown, spunbond/meltblown/spunbond, carded and thermobonded or bonded by some other means known in the art. The topsheet 30 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof.

Bi-component fibers may be made up of a polyester layer and a polyethylene sheath. The use of appropriate bi-component materials results in a fusible nonwoven fabric. Using a fusible fabric increases the ease with which the topsheet 30 may be mounted to the adjacent absorbent system 50 and/or to the backsheet 40.

The topsheet 30 preferably has a relatively high degree of wettability, although the individual fibers comprising the cover may not be particularly hydrophilic. The topsheet material may also contain a great number of relatively large pores. This is because the topsheet 30 is intended to take-up body fluid rapidly and transport it away from the body and the point of deposition. Therefore, the topsheet 30 contributes little to the time taken for the napkin to absorb a given quantity of liquid (penetration time). Advantageously, the fibers which make up the topsheet 30 should not lose their physical properties when they are wetted, in other words they should not collapse or lose their resiliency when subjected to water or body fluid. The topsheet 30 may be treated to allow fluid to pass through it readily. The topsheet 30 also functions to transfer the fluid quickly to the other layers of the absorbent pad 1. Thus, the topsheet 30 is advantageously wettable, hydrophilic and porous. When composed of synthetic hydrophobic fibers such as polypropylene and polyethylene or bi-component fibers, the topsheet 30 may be treated with a surfactant to impart the desired degree of wettability.

Alternatively, the topsheet 30 can also be made of polymer film having large pores. Because of such high porosity, the film accomplishes the function of quickly transferring body fluid to the inner layers of the absorbent pad 1.

The topsheet 30 may be embossed to the layers of the absorbent system 50 in order to aid in promoting hydrophilicity by fusing the topsheet 30 to the immediately adjacent layer of the absorbent system 50. Such fusion may be effected locally, at a plurality of sites or over the entire contact surface of the topsheet 30. Alternatively, the topsheet 30 may be attached to the absorbent system 50 by other means such as by adhesion.

The absorbent system 50 may be made up of an acquisition/distribution layer (ADL) 52 and an absorbent core 54 disposed below the ADL 52. The ADL 52 receives body fluid from the topsheet 30 and holds it until the underlying absorbent core 54 has an opportunity to absorb the fluid.

The ADL 52 may be more dense and have a larger proportion of smaller pores than the topsheet 30. These attributes allow the ADL 52 to contain body fluid and hold it away from the outer side of the topsheet 30, thereby preventing the fluid from re-wetting the topsheet 30 and its surface. However, the ADL 52 is not so dense as to prevent the passage of the fluid through the ADL 52 into the underlying absorbent core 54. The ADL 52 should transmit liquid quickly to the absorbent core 54 and move the liquid along the length of the core 54. The ADL 52 may be an apertured film comprised of a polyolefin that is rendered wettable by the use of a hydrophilic additive.

The ADL 52 may be composed of fibrous materials, such as wood pulp, polyester, rayon, flexible foam, or the like, or combinations thereof. The ADL 52 may also comprise thermoplastic fibers for the purpose of stabilizing the layer and maintaining its structural integrity. The ADL 52 may be treated with surfactant on one or both sides in order to increase its wettability, although generally the ADL 52 is relatively hydrophilic and may not require treatment. The ADL 52 is preferably bonded on both sides to the adjacent layers, i.e. the topsheet 30 and the underlying absorbent core 54.

The absorbent core 54 may be composed of a blend or mixture of cellulosic fibers and superabsorbent disposed in and amongst the fibers. Cellulosic fibers that may be used in the absorbent core 54 are well known in the art and include wood pulp, cotton, flax and peat moss. The absorbent core 54 may contain any superabsorbent polymer (SAP), which SAPs are well known in the art. The superabsorbent polymer particles may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. The absorbent core 54 may be made up of multiple layers of absorbent material, and may further include one or more layers of tissue.

In a specific example, the absorbent core 54 is a material containing from about 50 to about 90 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP. The absorbent core 54 can be manufactured by using air-laying means well known in the art.

The absorbent core 54 may be made up of two or more layers. For example, the absorbent core 54 may be composed of a first core that is rectangular and a second core that is contoured.

Now that the preferred embodiments of the present invention have been shown and described in detail, various modifications and improvement thereon will become readily apparent to those skilled in the art. Accordingly, the spirit and scope of the present invention is to be construed broadly and limited only by the appended claims, and not by the foregoing specification.

What is claimed is:

1. An absorbent pad comprising:
   a main body having a first lateral edge, a second lateral edge, a first longitudinal edge, a second longitudinal edge, a longitudinal width extending from the first lateral edge to the second lateral edge, and a lateral width extending from the first longitudinal edge to the second longitudinal edge, the main body comprising:
   a liquid pervious topsheet;
   a liquid impervious backsheet comprising an inner backsheet and an outer backsheet, the outer backsheet having a longitudinal width that is less than the longitudinal width of the main body and a lateral width that is greater than the lateral width of the main body;
   an absorbent system disposed between the topsheet and the backsheet;
   a central adhesive element disposed on the backsheet and extending along a longitudinal centerline of the absorbent pad; and
   an elastic element disposed along each of the first and second longitudinal edges of the main body and attached to at least one of the topsheet and the backsheet, the elastic element being disposed below the entire topsheet and above the entire backsheet so as to be layered between the topsheet and the backsheet;
   a first wing element formed of the outer backsheet and having a longitudinal width that is equal to the longitudinal width of the outer backsheet, the first wing element extending laterally beyond the first longitudinal edge of the main body; and
   a second wing element formed of the outer backsheet and having a longitudinal width that is equal to the longitudinal width of the outer backsheet, the second wing element extending laterally beyond the second longitudinal edge of the main body, the first and second wing elements being releasably attachable to an undergarment.

2. The absorbent pad of claim 1, further comprising a peel strip that covers the central adhesive.

3. The absorbent pad of claim 1, wherein the absorbent system comprises an absorbent core.

4. The absorbent pad of claim 3, wherein the absorbent system comprises an acquisition/distribution layer disposed over the absorbent core.

5. The absorbent pad of claim 3, wherein the absorbent core comprises at least one of cellulosic fibers and superabsorbent material.

6. The absorbent pad of claim 1, wherein the inner backsheet comprises a polymeric film layer.

7. The absorbent pad of claim 1, wherein the outer backsheet comprises a nonwoven material.

8. The absorbent pad of claim 1, wherein the topsheet comprises a nonwoven material.

9. A method of forming an absorbent pad, comprising the steps of:
   forming a liquid pervious topsheet from a topsheet material web;
   forming a liquid impervious backsheet comprising an inner backsheet and an outer backsheet from backsheet material webs;
   forming a main body comprising an absorbent system disposed between the backsheet and the topsheet, the main body having a first lateral edge, a second lateral edge, a first longitudinal edge, a second longitudinal edge, a longitudinal width extending from the first lateral edge to the second lateral edge, and a lateral width extending from the first longitudinal edge to the second longitudinal edge;
   cutting the outer backsheet so that the outer backsheet has a longitudinal width that is less than the longitudinal width of the main body and a lateral width that is greater than the lateral width of the main body;
   attaching an elastic element to at least one of the topsheet and the backsheet along each of the first and second longitudinal edges of the main body and below the entire topsheet and above the entire backsheet so as to be layered between the topsheet and the backsheet, the elastic elements generating a cupping action so that the absorbent pad is biased towards a cup-like shape;
   attaching a central adhesive element to the backsheet along a longitudinal centerline of the absorbent pad;
   forming a first wing element from the outer backsheet having a longitudinal width that is equal to the longitudinal width of the outer backsheet, the first wing element extending laterally beyond the first longitudinal edge of the main body, and
   forming a second wing element from the outer backsheet having a longitudinal width that is equal to the longitudinal width of the outer backsheet, the second wing element extending laterally beyond the second longitudinal edge of the main body.

10. The method of claim 9, further comprising the step of covering the central adhesive element with a central peel strip.

11. The method of claim 9, wherein the step of forming the main body comprises laminating the topsheet, backsheet and absorbent system together to form a unitary structure.

12. The method of claim 9, wherein the absorbent system comprises an absorbent core.

13. The method of claim 12, wherein the absorbent system comprises an acquisition/distribution layer disposed over the absorbent core.

14. The method of claim 9, wherein the topsheet material comprises a nonwoven material layer.

* * * * *